(12) United States Patent
Tseng et al.

(10) Patent No.: US 10,444,233 B2
(45) Date of Patent: Oct. 15, 2019

(54) SELECTIVE CAPTURE AND STIMULATED RELEASE OF CIRCULATING TUMOR CELLS ON NANOSTRUCTURED DEVICES

(71) Applicants: The Regents of the University of California, Oakland, CA (US); RIKEN, Saitama (JP)

(72) Inventors: Hsian-Rong Tseng, Los Angeles, CA (US); Shuang Hou, Los Angeles, CA (US); Libo Zhao, Los Angeles, CA (US); Hsiao-Hua Yu, Saitama (JP); Shyh-Chyang Luo, Saitama (JP); Haichao Zhao, Saitama (JP)

(73) Assignees: The Regents of the University of California, Oakland, CA (US); Riken, Saitama (JP)

( * ) Notice: Subject to any disclaimer, the term of this patent is extended or adjusted under 35 U.S.C. 154(b) by 149 days.

(21) Appl. No.: 14/418,406

(22) PCT Filed: Jul. 31, 2013

(86) PCT No.: PCT/US2013/053063
§ 371 (c)(1),
(2) Date: Jan. 29, 2015

(87) PCT Pub. No.: WO2014/022581
PCT Pub. Date: Feb. 6, 2014

(65) Prior Publication Data
US 2015/0260710 A1 Sep. 17, 2015

Related U.S. Application Data

(60) Provisional application No. 61/677,825, filed on Jul. 31, 2012.

(51) Int. Cl.
*G01N 33/543* (2006.01)
*G01N 25/18* (2006.01)
*G01N 33/545* (2006.01)

(52) U.S. Cl.
CPC ..... *G01N 33/545* (2013.01); *G01N 33/54306* (2013.01); *G01N 33/54346* (2013.01); *G01N 2333/70596* (2013.01)

(58) Field of Classification Search
CPC ........ G01N 25/30; G01N 25/34; G01N 25/18; G01N 27/14; G01N 30/54
See application file for complete search history.

(56) References Cited

U.S. PATENT DOCUMENTS 9,140,697 B2 * 9/2015 Tseng ................ B01L 3/502707

FOREIGN PATENT DOCUMENTS

| CN | 1569933 A | 1/2005 |
|---|---|---|
| CN | 101037510 A | 9/2007 |

(Continued)

OTHER PUBLICATIONS

Tajima et al., "A Novel Interface for High-Sensitive Immunoassay Using Orientation Controlled Protein A and Non-biofouling Phospholipid Polymer Surface", vol. 34 [2], pp. 205-208, published 2009.*

(Continued)

*Primary Examiner* — Tracy Vivelmore
*Assistant Examiner* — Nam P Nguyen
(74) *Attorney, Agent, or Firm* — Venable LLP; Henry J. Daley; Miguel A. Lopez

(57) ABSTRACT

A device for capturing preselected cell types from a fluid sample that includes a plurality of cell types includes a substrate, a plurality of nanowires at least one of attached to or integral with a surface of the substrate such that each nanowire of the plurality of nanowires has an unattached (Continued)

end, and a layer of temperature-responsive material formed on at least the unattached end of each of the plurality of nanowires. The layer of temperature-responsive material has a compact configuration at a first temperature and an expanded configuration at a second temperature so as to facilitate release of cells captured at the first temperature to be released at the second temperature.

16 Claims, 9 Drawing Sheets

(56) References Cited

FOREIGN PATENT DOCUMENTS

| CN | 101289522 A | 10/2008 |
|----|-------------|---------|
| CN | 102405411 A | 4/2012 |
| WO | WO-96/27132 A1 | 9/1996 |
| WO | WO-2010/108003 A2 | 9/2010 |

OTHER PUBLICATIONS

Wikipedia.com, "Standard conditions for temperature and pressure", https://en.wikipedia.org/wiki/Standard_conditions_for_temperature_and_pressure, print retrieved Apr. 2, 2017.*
Kim et al.,"Swelling Induced Detachment of Chondrocytes Using RGD-Modified Poly(N-isopropylacrylamide) Hydrogel Beads", Biotechnol. Prog., vol. 18, pp. 495-500, published Jun. 7, 2002. (Year: 2002).*
Kim et al., "Mimicking dynamic in vivo environments with stimuli-responsive materials for cell culture," Trends in Biotechnology, 2012, vol. 30, No. 8, pp. 426-439.
Cole et al., "Stimuli-responsive interfaces and systems for the control of protein-surface and cell-surface interactions," Biomaterials, 2006, vol. 30, No. 9, pp. 1827-1850.
Adams et al., J Am Chem Soc 2008, 130, 8633-8641.
Chen et al., Journal of the American Chemical Society 2009, 131, 10467-10472.
Chen et al., *Adv Mater* 2011, 23, 43764380.
Chung et al., Journal of Controlled Release 1999, 62, 115-127.
Cristofanilli et al., N Engl J Med 2004, 351, 781-791.
Curtis et al., Journal of the National Cancer Institute 1964, 33, 15-&.
Dharmasiri et al., Anal Chem 2011, 83, 2301-2309.
Dickson et al., Biomicrofluidics 2011, 5.
Fischer et al., *Nano Letters* 2009, 9, 716-720.
Gleghom et al., Lab Chip 2010, 10, 27-29.
Kim et al., Nanoscale 2012, 4, 2500-2507.
Kumashiro et al., Annals of Biomedical Engineering 2010, 38, 1977-1988.
Liu et al., Advanced Drug Delivery Reviews 2007, 59, 1319-1328.
Nagrath et al., Nature 2007, 450, 1235-1239.
Nishida et al., New England Journal of Medicine 2004, 351, 1187-1196.
Okano et al., Biomaterials 1995, 16, 297-303.
Pantel et al., Trends Mol Med 2010, 16, 398-406.
Pantel et al., Nat Rev Cancer 2008, 8, 329-340.
Pantel et al., Nat Rev Cancer 2004, 4, 448-456.
Racila et al., Proceedings of the National Academy of Sciences of the United States of America 1998, 95, 4589-4594.
Riethdorf et al., Clin Cancer Res 2007, 13, 920-928.
Sekine et al., Adv Mater 2011, 23, 4788-4792.
Shaffer et al., Clin Cancer Res 2007, 13, 2023-2029.
Stott et al., Proc Nati Acad Sci U S A 2010, 107, 18392-18397.
Turan et al., Thin Solid Films 2010, 518, 5950-5954.
Wang et al., Angew Chem Int Ed Engl 2009, 48, 8970-8973.
Wang et al., Angew Chem Int Ed Engl 2011, 50, 3084-3088.
Went et al., Human Pathology 2004, 35, 122-128.
Yu et al., Langmuir 2010, 26, 8582-8588.
Zhang, et al., Adv Mater 2012, 24, in press.
Zieglschmid et al., Crit Rev Clin Lab Sci 2005, 42, 155-196.
Li et al., "Fabrication of thermoresponsive polymer gradients for study of cell adhesion and detachment," Langmuir, 2008, vol. 24, pp. 13632-13639.
Cole et al., "Stimuli-responsive interfaces and systems for the control of protein-surface and cell-surface interactions," Biomaterials, 2009, vol. 39, pp. 1827-1850.
Brun-Graeppi et al., "Thermoresponsive surfaces for cell culture and ensyme-free cell detachment," Progress in Polymer Science, 2010, vol. 35, pp. 1311-1324.
Zhou et al., "A temperature-responsive antibody-like nanostructure," Biomacromolecules, 2010, vol. 8, pp. 2087-2093.
Hou et al., Capture and Stimulated Release of Circulating Tumor Cells on Polymer-Grafted Silicon Nanostructures,: Advanced Materials, 2013, vol. 25, pp. 1547-1551.
Okamura et al., "Poly(N-isopropylacrylamide)-graft-polypropylene membranes containing adsorbed antibody for cell separation," Biomaterials 26(2005): pp. 1287-1292.

* cited by examiner

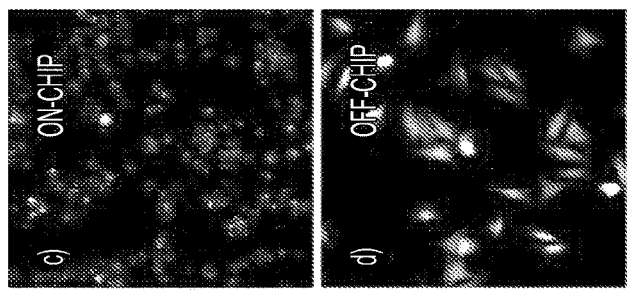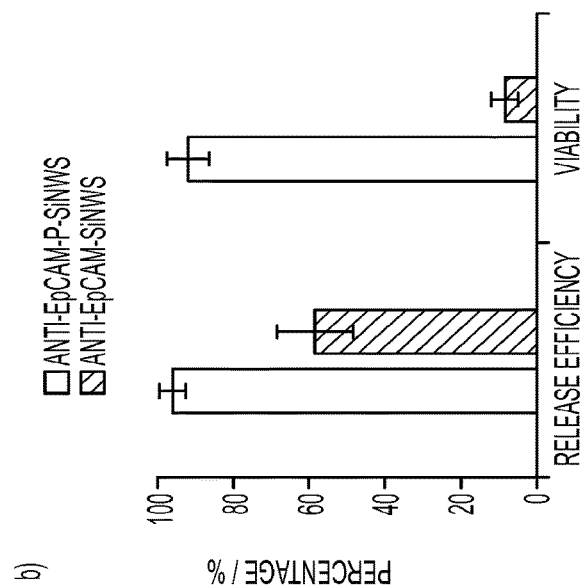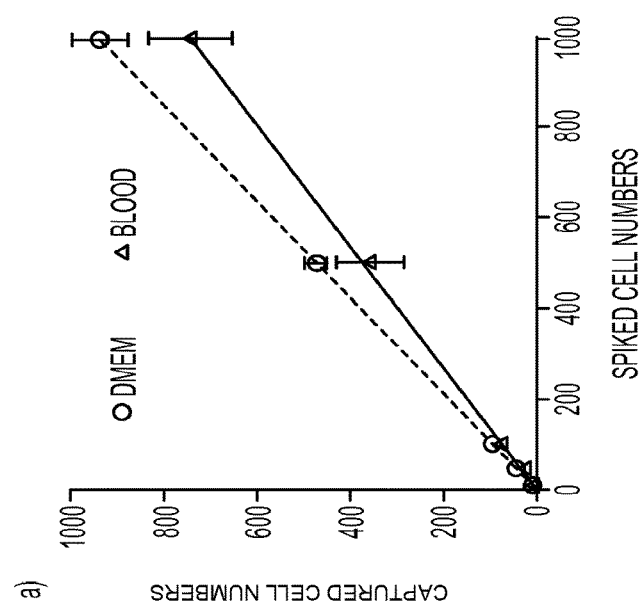
FIG. 6A-6D

SELECTIVE CAPTURE AND STIMULATED RELEASE OF CIRCULATING TUMOR CELLS ON NANOSTRUCTURED DEVICES

CROSS-REFERENCE OF RELATED APPLICATION

This is a national stage application under 35 U.S.C. § 371 of PCT/US2013/053063 filed Jul. 13, 2013, the entire contents of which are incorporated herein by reference and this application claims priority to U.S. Provisional Application No. 61/677,825 filed Jul. 31, 2012, the entire contents of which are hereby incorporated by reference.

This invention was made with Government support under Grant Nos. CA151159 and CA157396, awarded by The National Institutes of Health (NIH). The Government has certain rights in the invention.

BACKGROUND

1. Field of Invention

The field of the currently claimed embodiments of this invention relates to devices and methods for selective capture and stimulated release of circulating cells.

2. Discussion of Related Art

Circulating tumor cells[1] (CTCs) are cancer cells that shed away from either primary tumor(s) or metastatic sites, and circulate in the peripheral blood as the cellular origin of metastases[2]. The current gold standard for cancer diagnosis requires invasive biopsy and subsequent histopathology analysis of the biopsy samples. However, in early stage metastasis or recurrence, it is difficult to identify the metastatic/recurrence sites for collection tissue biopsies. CTCs can therefore be regarded as a "liquid biopsy" of the tumor that offers convenient access to tumor cells before fatal metastasis occurs. To exploit CTCs as a new cancer "biomarker" that could report disease progression and guide implementation of therapy, significant research endeavors[3] have been devoted to developing diagnostic assays capable of detecting and enumerating CTCs in cancer patients' blood. The major technical challenge is to efficiently and specifically capture the extremely low abundance (a few to hundreds cells/mL) of CTCs among a high number ($10^9$ cells/mL) of hematologic cells[4] in blood samples. Based on different working mechanisms, a diversity of CTC assays has been created over the past decades. For example, immunomagnetic separation approaches[5] utilize magnetic beads coated with CTC-specific capture agents (e.g., antibodies or aptamers) to capture CTCs. CellSearch™ Assay based on the immunomagnetic separation is the only FDA-cleared CTC enumeration method that can predict prognostic outcomes in metastatic breast, prostate and colorectal cancer. Recently, there have been several microchip-based technologies[6] developed to address the concerns of low CTC-capture efficiency encountered by CellSearch™ Assay. At this juncture, an increasing number of new CTC assays have demonstrated their profound sensitivity for CTC enumeration in cancer patients. In order to further exploit the diagnostic values of CTCs beyond enumeration, current research enterprises are dedicated for establishing molecular and functional analyses of CTCs. It is conceivable that the CTC-derived molecular signatures and functional readouts will provide valuable insight into tumor biology during the critical window where therapeutic intervention could make a significant difference. To pave the way toward molecular and functional analyses of CTCs, there is a desperate need to develop a new CTC assay that can not only capture CTCs with high efficiency, but also release CTCs with minimum contamination of the surrounding white blood cells (WBCs) and negligible disruption to CTCs' viability and functions.

SUMMARY

A device for capturing preselected cell types from a fluid sample that includes a plurality of cell types according to an embodiment of the current invention includes a substrate, a plurality of nanowires at least one of attached to or integral with a surface of the substrate such that each nanowire of the plurality of nanowires has an unattached end, and a layer of temperature-responsive material formed on at least the unattached end of each of the plurality of nanowires. The layer of temperature-responsive material has a compact configuration at a first temperature and an expanded configuration at a second temperature so as to facilitate release of cells captured at the first temperature to be released at the second temperature.

A method of capturing preselected cell types from a fluid sample that includes a plurality of cell types according to an embodiment of the current invention includes providing a temperature-responsive, nanostructured cell capture device; depositing a sample onto a cell capture surface of the temperature-responsive, nanostructured cell capture device; changing a temperature of the temperature-responsive, nanostructured cell capture device to facilitate removal of viable captured cells; and collecting captured cells subsequent from removal from the temperature-responsive, nanostructured cell capture device.

BRIEF DESCRIPTION OF THE DRAWINGS

Further objectives and advantages will become apparent from a consideration of the description, drawings, and examples.

FIGS. 6A-6D provide data for a) Cell-capture efficiency at different cell numbers ranging from 10-1000 cells mL-1 in three different types of samples: DMEM medium (□) and whole blood (Δ). b) Cell-release performance and the viability of released cells observed for MCF7 cell capture/release studies using anti-EpCAM-coated biotin-P-SiNWS (white bars) and SiNWS (black bars). c) DiO-stained MCF7 cells were successfully cultured after capture and released from anti-EpCAM-coated biotin-P-SiNWS.

DETAILED DESCRIPTION

Figure 1A:
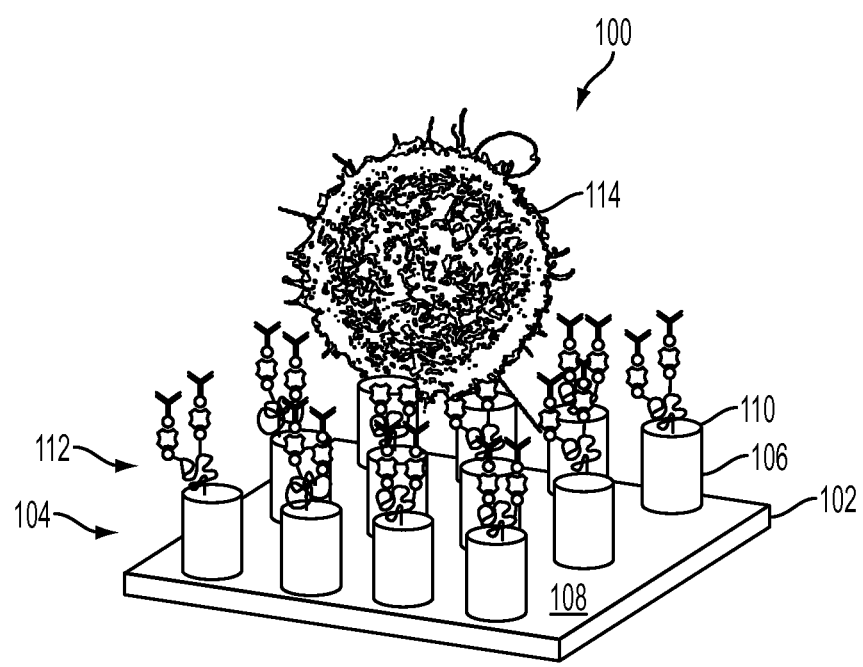
FIGS. 1A and 1B provides schematic views of a device for capturing preselected cell types from a fluid sample that includes a plurality of cell types according to an embodiment of the current invention.

Some embodiments of the current invention are discussed in detail below. In describing embodiments, specific terminology is employed for the sake of clarity. However, the invention is not intended to be limited to the specific terminology so selected. A person skilled in the relevant art will recognize that other equivalent components can be employed and other methods developed without departing from the broad concepts of the current invention. All references cited anywhere in this specification, including the Background and Detailed Description sections, are incorporated by reference as if each had been individually incorporated.

A "temperature-responsive material" or "thermally responsive material" or "thermoresponsive material" is any material that exhibits a response to a change in temperature, e.g., one or more properties of the material changes as the temperature changes. A temperature-responsive material generally undergoes a substantial and discontinuous change in one or more properties. The change in property can occur at or near a critical temperature. The property that undergoes the substantial and discontinuous change can be solubility. Other properties related to solubility can also undergo substantial and discontinuous changes.

A temperature-responsive material can include a temperature-responsive polymer. The temperature-responsive behavior of the temperature-responsive material can be imparted by the temperature-responsive behavior of the temperature-responsive polymer.

A "temperature-responsive polymer" or "thermally responsive polymer" or "thermoresponsive polymer" is a polymer that undergoes a substantial change in one or more properties in response to a change in temperature. One such property can be solubility in a particular solvent, e.g., water, or an aqueous solution. The change in solubility can be related to a change in intra- and inter-molecular interactions within and between polymer molecules. For example, under some conditions (depending on factors including the nature of the polymer, the nature of the solvent, the polymer concentration, and temperature), it may be energetically favorable for the polymer molecules to self-associate. Under other conditions, interactions with solvent will be energetically favorable. A "temperature-responsive polymer" includes thermally responsive polymer brushes. A "polymer brush" refers to a polymer that is attached or grafted to a surface, e.g., a linear polymer where one end of the polymer chain is attached (for example, covalently grafted) to a surface.

In some embodiments, the temperature-responsive polymer can be characterized with reference to an upper critical solution temperature (UCST) and/or a lower critical solution temperature (LCST). In a given solvent, the temperature-responsive polymer is miscible with the solvent at all concentrations when the temperature is above the LCST but below the UCST.

With regard to LCST, when the temperature of a solution is raised above the phase separation temperature the hydrophobic backbone and other nonpolar groups of the polymer tend to associate. This causes intra- and intermolecular aggregation leading to collapse of the individual polymer chains and precipitation of the polymer.

Thus in some embodiments, a temperature-sensitive material can undergo a change in solvent miscibility in response to a change in temperature. The change in solvent miscibility can be associated with a change in polymer conformation, such as a coil-globule transition, e.g., between polymer molecules favoring more extended conformations that reduce intra- and inter-molecular interactions within and between polymer molecules, and more compact conformations that promote intra- and inter-molecular interactions within and between polymer molecules.

The term "alkyl" used alone or as part of a larger moiety (i.e. "alkoxy," "hydroxyalkyl," "alkoxyalkyl," and "alkoxycarbonyl") includes both straight and branched chains containing one to ten carbon atoms (i.e. 1, 2, 3, 4, 5, 6, 7, 8, 9, or 10 carbon atoms), as well as cyclic structures such as cyclopropyl and cyclobutyl. Examples of alkyl groups include methyl (Me), ethyl (Et), propyl (Pr) (including n-propyl ("Pr or n-Pr), isopropyl ($^i$Pr or i-Pr) and cyclopropyl ($^c$Pr or c-Pr)), butyl (Bu) (including n-butyl ("Bu or n-Bu), isobutyl ($^i$Bu or i-Bu), tert-butyl ($^t$Bu or t-Bu) and cyclobutyl ($^c$Bu or c-Bu)), pentyl (Pe) (including n-pentyl) and so forth. Alkyl groups also include mixed cyclic and linear alkyl groups, such as cyclopentylmethyl, cyclopentylethyl, cyclohexylmethyl, etc., so long as the total number of carbon atoms is not exceeded. The term "alkyl" also refers to structures that are optionally substituted.

The term "heterocycle", "heterocyclyl", or "heterocyclic" unless otherwise indicated includes non-aromatic ring systems having five to fourteen members, preferably five to ten, in which one or more ring carbons, preferably one to four, are each replaced by a heteroatom such as N, O, or S. Examples of heterocyclic rings include 3-1H-benzimidazol-2-one, (1-substituted)-2-oxo-benzimidazol-3-yl, 2-tetrahydrofuranyl, 3-tetrahydrofuranyl, 2-tetrahydropyranyl, 3-tetrahydropyranyl, 4-tetrahydropyranyl, [1,3]-dioxalanyl, [1,3]-dithiolanyl, [1,3]-dioxanyl, 2-tetrahydrothiophenyl, 3-tetrahydrothiophenyl, 2-morpholinyl, 3-morpholinyl, 4-morpholinyl, 2-thiomorpholinyl, 3-thiomorpholinyl, 4-thiomorpholinyl, 1-pyrrolidinyl, 2-pyrrolidinyl, 3-pyrrolidinyl, 1-piperazinyl, 2-piperazinyl, 1-piperidinyl, 2-piperidinyl, 3-piperidinyl, 4-piperidinyl, 4-thiazolidinyl, diazolonyl, N-substituted diazolonyl, 1-phthalimidinyl, benzoxanyl, benzopyrrolidinyl, benzopiperidinyl, benzoxolanyl, benzothiolanyl, and benzothianyl. Also included within the scope of the term "heterocyclyl" or "heterocyclic", as it is used herein, is a group in which a non-aromatic heteroatom-containing ring is fused to one or more aromatic or non-aromatic rings, such as in an indolinyl, chromanyl, phenanthridinyl, or tetrahydroquinolinyl, where the radical or point of attachment is on the non-aromatic heteroatom-containing ring. The term "heterocycle", "heterocyclyl", or "heterocyclic" whether saturated or partially unsaturated, also refers to rings that are optionally substituted. The term "heterocyclylalkyl" refers to an alkyl group substituted by a heterocyclyl.

The term "substituted" refers to a chemical structure where a hydrogen atom has been replaced by a substituent. A "substituent" is a chemical structure that replaces a hydrogen atom on the substituted structure. The term "substituent" does not imply that the substituent is smaller than the substituted structure. "Substituents" include, but are not limited to, groups such as halogen, alkyl, alkenyl, nitro, hydroxyl, alkoxy, alkylthio, amino, alkylamino, dialkylamino, aminocarbonyl, alkylaminocarbonyl, dialkylaminocarbonyl, alkylaminocarbonyloxy, dialkylaminocarbonyloxy, carboxy, alkoxycarbonyl, alkylcarbonyl, aryl, heteroaryl, and heterocycle.

In contrast to conventional approaches for CTC enrichment, the current inventors previously provided a NanoVelcro cell-affinity assay, by which anti-EpCAM[7] (epithelial cell adhesion molecule)-coated nanostructured substrates (e.g., vertically oriented silicon nanowire substrates, SiNWS) were utilized to capture CTCs in a stationary device setting[8] with a capture efficiency ranging from 40 to 70%. (See, for example, U.S. Published Patent Application No. US 2012/0003711 A1, "Device for Capturing Circulating Tumor Cells," assigned to the same assignee as the current application, the entire contents of which are incorporated herein by reference.) A novel feature of our NanoVelcro CTC assay is the use of a nanostructured substrate. The enhanced local topographic interactions[9] between the SiNWS and nano-scaled cellular surface components (e.g., microvilli) are analogous to the working principle of nanoscale VELCRO, resulting in a vastly improved cell-capture affinity compared to that observed for non-structured (i.e., flat) substrates. The general applicability of the NanoVelcro concept is supported by i) our recent studies, where we demonstrated that other types of nanostructured substrates, e.g., electrochemically deposited conjugated polymer nano-features,[10] and horizontally packed ultra-long TiO2 nanofibers[11], also exhibit synergistic effects in conjunction with capture agents to achieve enhanced CTC-capture performance, and ii) others' studies[12], where immune cell-specific capture agent-coated SiNWS were utilized to sort subpopulations of immune cells. (See also "Systems, Methods and Components for Isolating Cells from a Fluid Sample," PCT/US13/43171, filed May 29, 2013, assigned to the same assignee as the current application, the entire contents of which are incorporated herein by reference.) Although the NanoVelcro cell-affinity assay exhibited enhanced cell capture performance, it proved difficult to release the immobilized cells (via enzymatic treatment) from capture agent-coated substrates. In some examples, only 10% of viable cells were released, and poor cell viability was observed.

Accordingly, some embodiments of the current invention can provide an improvement over the previous NanoVelcro cell-affinity assay that is capable of not only capturing CTCs with high efficiency, but also releasing the nanosubstrate-immobilized CTCs at a lower temperature. However, the general concepts of the current invention are not limited to only this embodiment.

Figure 1B:
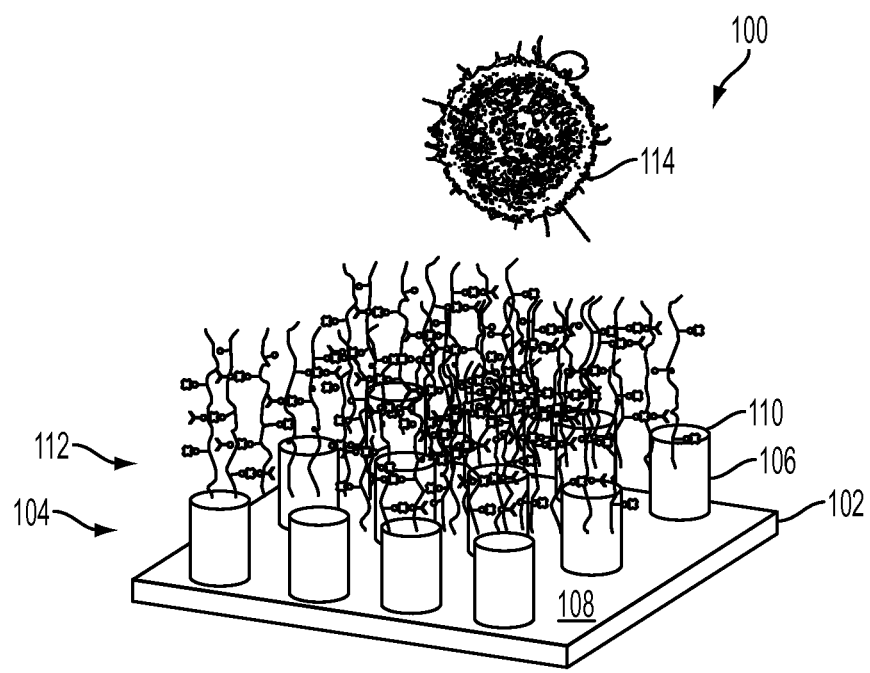

FIGS. 1A and 1B are schematic illustrations to help explain some concepts of the current invention. FIGS. 1A and 1B provide a schematic illustration of a device 100 for capturing preselected cell types from a fluid sample that includes a plurality of cell types according to an embodiment of the current application. The device 100 includes a substrate 102, and a plurality of nanowires 104 (e.g., one of which is labeled 106) at least one of attached to or integral with a surface 108 of the substrate 102 such that each nanowire (e.g., 106) of the plurality of nanowires 104 has an unattached end 110. The device 100 also includes a layer of temperature-responsive material 112 formed on at least the unattached end of each of the plurality of nanowires 104. The layer of temperature-responsive material 112 has a compact configuration (FIG. 1A) at a first temperature and an expanded configuration (FIG. 1B) at a second temperature so as to facilitate release of cells 114 captured at the first temperature to be released at the second temperature.

The term nanowire is intended to include a nanostructure that has a longitudinal dimension that is greater than the two orthogonal lateral dimensions. The two lateral dimensions are both less than 1 μm. The longitudinal dimension can be less than 1 μm in some embodiments, or can be greater than 1 μm in some embodiments. The term nanowire is intended to have a broad definition such that it can include nanofibers or nanopillars in some embodiments. In some embodiments, the nanowires 112 can be oriented vertically as depicted in FIGS. 1A and 1B. However, the general concepts of the current invention are not limited to only this example. In some embodiments, the nanowires 112 can be produced by semiconductor processing techniques such as, but not limited to, photolithographic exposure and etching, and/or epitaxial growth techniques. In some embodiments, the substrate and/or nanowires can be a semiconductor, such as, but not limited to, silicon. In some embodiments, the nanowires can be an oxide, such as, but not limited to $SiO_2$ or $TiO_2$, for example. In some embodiments the nanowires can be a thermal plastic material or other material with similar mechanical properties.

FIGS. 1A and 1B illustrate an example of the layer of temperature-responsive material 112 formed on the unattached end of each of the plurality of nanowires 104. However, this does not preclude embodiments in which some temperature-responsive material is attached to sides of the plurality of nanowires and/or on the surface 108. In addition the layer of temperature-responsive material 112 can each be separate from the others, or there could be some overlap. In some embodiments, the layer of temperature-responsive material 112 are substantially separate from adjacent layers such that the topological structure of the nanowires can play a role in the capture of the cells.

In some embodiments, the first and second temperatures are both greater than freezing temperature of water and less than boiling temperature of water at about one atmosphere of pressure. In some embodiments, the first and second temperatures are both within a range of temperature to maintain viability of captured and released cells.

In some embodiments, each of the plurality of nanowires 104 has an average diameter that is less than 500 nanometers. Although the nanowires are illustrated as having approximately circular cross-sectional shapes, the plurality of nanowires 104 are not limited to only those structures. However, regardless of the cross-section shape of a particular nanowire, it can be considered to have an effective diameter. For example, a cross-sectional area of any of the nanowires can be equated with the area of a circle to define an effective diameter. However, the broad concepts of the current invention are not limited to this example. In addition, the plurality of nanowires 104 can be substantially uniform, or they can vary due to either manufacturing tolerance and/or deliberated design. Similarly, the plurality of nanowires 104 can be considered to have an average diameter, or average effective diameter, to characterize the plurality of nanowires 104. Therefore, in some embodiments such an average diameter can be less than 500 nanometers. In some embodiments, the average diameter can be less than 250 nanometers and greater than 20 nanometers. In some embodiments, the average diameter can be within the inclusive range of 200 nanometers to 100 nanometers.

In some embodiments, the device 100 can further include at least one type of cell-selective binding molecule attached to a plurality of portions of the layer of temperature-responsive material formed on each of the plurality of nanowires. In some embodiments, the at least one type of cell-selective binding molecule can attached to the layer of temperature-responsive material by at least one of biotin or streptavidin conjugation.

In some embodiments, the cell-selective binding molecule binds to circulating cancer cells (CTCs) preferentially over other cell types of the plurality of cell types. The cell-selective binding molecule can include an antibody for CTC capture. For example, the antibody CTC capture can include at least one of EpCAM, CA19-9, CD146, or CD147 antibodies.

In some embodiments, the cell-selective binding molecule binds to fetal nucleated red blood cells (fNRBCs) from maternal blood preferentially over other cell types of the plurality of cell types. In this case, the cell-selective binding molecule can include at least one of CD71 or CD147 antibodies for the capture of fetal nucleated red blood cells (fNRBCs) from maternal blood.

In some embodiments, the layer of temperature-responsive material formed on at least the unattached end of each of the plurality of nanowires can include a temperature-responsive polymer. In some embodiments, the temperature-responsive polymer can include a monomer unit of one of formulas (I)-(VI):

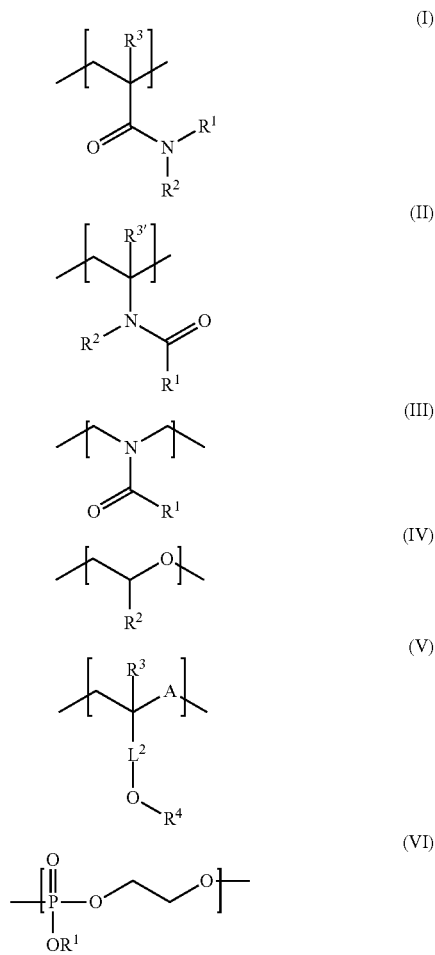

In formulas (I)-(VI), $R^1$ can be optionally substituted $C_1$-$C_6$ alkyl or optionally substituted $C_3$-$C_8$ cycloalkyl, and $R^2$ can be H, optionally substituted $C_1$-$C_6$ alkyl, or optionally substituted $C_3$-$C_8$ cycloalkyl; or, in some embodiments, $R^1$ and $R^2$ taken together with the atom(s) to which they are attached can form a 5-8 membered optionally substituted heterocycle, where the heterocycle includes at least one N and optionally one to three additional heteroatoms selected from O, N, and S.

$R^3$ can be H or $C_1$-$C_3$ alkyl. $R^{3'}$ can be H, $C_1$-$C_3$ alkyl, or —$CO_2R^{4'}$. $R^4$ can be H, $C_1$-$C_3$ alkyl, —C(O)—$C_1$-$C_3$ alkyl, or —$(CH_2CH(R^{4'})O)_y$—$R^{4'}$. $L^2$ can be —$(CH_2)_x$— or —C(=O)—. Each $R^{4'}$ independently can be H or optionally substituted $C_1$-$C_3$ alkyl. x can be from 0 to 3; and y can be from 0 to 10.

The temperature-responsive polymer can be covalently grafted to at least said unattached end of each of said plurality of nanowires. The temperature-responsive polymer can include a monomer unit that is suitable for attaching a cell-selective binding molecule thereto.

In some embodiments, the temperature-responsive polymer can be a homopolymer of monomer units of formula (I), formula (II), formula (III), formula (IV), formula (V), or formula (VI). In some embodiments, the temperature-responsive polymer can be a copolymer. The copolymer can include two or more different monomer units; for example, the copolymer can include two or more monomer units having different structures, where the two or more monomer units are each of formula (I), each of formula (II), each of formula (III), each of formula (IV), each of formula (V), or each of formula (VI). In some embodiments, the copolymer includes two or more monomer units having different structures, selected from one or more of formulas (I)-(VI). In some embodiments, the copolymer can include at least one monomer unit of formula (I), formula (II), formula (III), formula (IV), formula (V), or formula (VI), and at least one monomer unit having a different structure, e.g., of formula (VII) described below.

Some temperature-responsive polymers which include monomer units of formulas (I)-(VI) are described in, for example, Aseyev, V., et al., *Adv. Polym. Sci.* 2011, 242, 29-89, which is incorporated by reference in its entirety.

In some embodiments, a temperature-responsive polymer includes a monomer unit of formula (I):

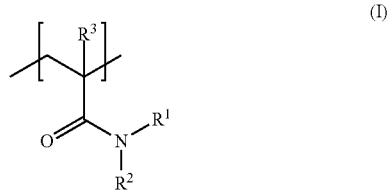

(I)

In some embodiments, $R^1$ can be optionally substituted $C_1$-$C_6$ alkyl and $R^2$ can be optionally substituted $C_1$-$C_6$ alkyl. In some cases, $R^1$ can be unsubstituted $C_1$-$C_6$ alkyl, and/or $R^2$ can be unsubstituted $C_1$-$C_6$ alkyl. In some cases, $R^3$ can be H or $CH_3$.

In some embodiments, $R^1$ and $R^2$ taken together with the atom(s) to which they are attached can form a 5-8 membered optionally substituted heterocycle, where the heterocycle includes at least one N and optionally one to three additional heteroatoms selected from O, N, and S. In some embodiments, the heterocycle can be substituted by one or more of OH and —$CO_2$—($C_1$-$C_6$ alkyl).

Examples of polymers of formula (I) include, but are not limited to, poly(N-alkyl(meth)acrylamide)s, N-monosubstituted and N-disubstituted poly(acrylamide)s, and N-monosubstituted and N-disubstituted poly(methacrylamide)s. Some examples include Poly(N-ethylacrylamide) (PEAAm), Poly(N-ethylmethacrylamide) (PEMAAm), Poly(N,N'-ethylmethylacrylamide) (PEMAAm), Poly(N,N'-diethylacrylamide) (PDEAAm), Poly(N-n-propylacrylamide) (PnPAAm), Poly(N-n-propylmethacrylamide) (PnPMAAm), Poly(N-isopropylacrylamide) (PiPAAm or PNIPAM), Poly(N-isopropylmethacrylamide) (PiPMAAm or PNIPMAm), Poly(N-cyclopropylacrylamide) (PcPAAm), Poly(N-(L)-(1-hydroxymethyl)propylmethacrylamide) (P(L-HMPMAAm)), Poly(N-acryloylpyrrolidine), Poly(N-acryloylpiperidine) (PAOPip), Poly(N-acryloyl-L-proline methyl ester) (PAProMEs), Poly(N-acryloyl-4-trans-hydroxy-L-proline methyl ester) (PAHProMEs), Poly(N-methylacrylamide) (PMAAm), Poly(N,N'-dimethylacrylamide) (PDMAAm), Poly(N-acrylylglycinamide), and Poly(N-methacrylylglycinamide).

In some embodiments, a temperature-responsive polymer includes a monomer unit of formula (II):

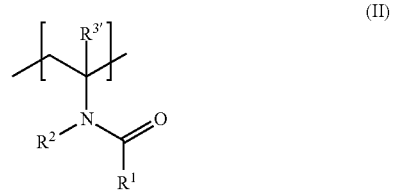

(II)

In some embodiments, $R^1$ can be optionally substituted $C_1$-$C_6$ alkyl and $R^2$ can be optionally substituted $C_1$-$C_6$ alkyl. In some cases, $R^1$ can be unsubstituted $C_1$-$C_6$ alkyl, and/or $R^2$ can be unsubstituted $C_1$-$C_6$ alkyl.

In some embodiments, $R^1$ and $R^2$ taken together with the atom(s) to which they are attached can form a 5-8 membered optionally substituted heterocycle, where the heterocycle includes at least one N and optionally one to three additional heteroatoms selected from O, N, and S. In some embodiments, $R^1$ and $R^2$ together are an optionally substituted $C_2$-$C_7$ alkylene or oxyalkylene chain.

In some embodiments, $R^1$ can be optionally substituted $C_1$-$C_6$ alkyl and $R^2$ can be H. In some cases, $R^1$ can be unsubstituted $C_1$-$C_6$ alkyl and $R^2$ can be H. $R^3$, can be —$CO_2R^{4'}$, where $R^{4'}$ can be H or $C_1$-$C_3$ alkyl. In some embodiments, $R^1$ can be unsubstituted $C_1$-$C_6$ alkyl, $R^2$ can be H, and $R^{3'}$ can be —$CO_2R^{4'}$, where $R^{4'}$ can be $C_1$-$C_3$ alkyl.

Examples of polymers of formula (II) include, but are not limited to, Poly(N-vinyl amide)s, Poly(N-vinyl caprolactam) (PVCL), Poly(N-vinyl propylacetamide), Poly(N-vinyl-5-methyl-2-oxazolidone), Poly(N-vinyl isobutyramide) (PViBAm), Poly(methyl 2-alkylamidoacrylate)s, poly(methyl 2-acetamidoacrylate), poly(methyl 2-propionamidoacrylate), poly(methyl 2-isobutyracrylate), poly(methyl 2-n-butyramidoacrylate), Poly(N-alkyl(meth)acrylamide)s bearing hydroxyl groups, N-monosubstituted and N-disubstituted poly(acrylamide)s, N-monosubstituted and N-disubstituted poly(methacrylamide)s, Poly(vinylpyrrolidone) (PVP), Poly(N-acryloylmorpholine) (pAOM), and Poly(N-tert-butylacrylamide).

In some embodiments, a temperature-responsive polymer includes a monomer unit of formula (III):

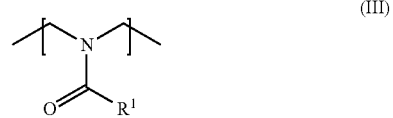

(III)

In some embodiments, $R^1$ can be optionally substituted $C_1$-$C_6$ alkyl. In some embodiments, $R^1$ can be unsubstituted $C_1$-$C_3$ alkyl.

Examples of polymers of formula (III) include, but are not limited to, Poly(oxazoline)s, Poly(2-methyl-2-oxazoline) (PMOz), Poly(2-methyl-2-oxazoline) (PMOz), Poly(2-n-propyl-2-oxazoline) (PnPOz), and Poly(2-isopropyl-2-oxazoline) (PiPOz), and Poly(2-substituted-2-oxazoline)s.

In some embodiments, a temperature-responsive polymer includes a monomer unit of formula (IV):

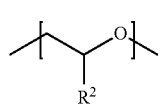

(IV)

In some embodiments, $R^2$ can be H or optionally substituted $C_1$-$C_6$ alkyl. In some embodiments, $R^2$ can be H or unsubstituted $C_1$-$C_3$ alkyl.

Examples of polymers of formula (IV) include, but are not limited to, Poly(ethyleneoxide) (PEO), which may also be referred to as poly(ethylene glycol) (PEG), and Poly(propyleneoxide) (PPO), which may also be referred to as poly(propylene glycol) (PPG).

In some embodiments, a temperature-responsive polymer includes a monomer unit of formula (V):

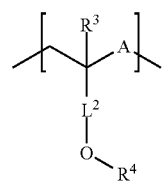

(V)

In some embodiments, A can be a single bond, $L^2$ can be —(CH$_2$)$_x$—, x can be 0, and $R^4$ can be —(CH$_2$CH(R$^{4'}$)O)$_y$—R$^{4'}$. In some embodiments, x can be 0 and $R^4$ can be —(CH$_2$CH$_2$O)$_y$—R$^{4'}$ where $R^{4'}$ can be $C_1$-$C_3$ alkyl.

In some embodiments, A can be a single bond, $L^2$ can be —(CH$_2$)$_x$—, x can be 0, and $R^4$ can be H or —C(O)—$C_1$-$C_3$ alkyl.

In some embodiments, A can be 0, $L^2$ can be —(CH$_2$)$_x$—, x can be 1, and $R^4$ can be H or —$C_1$-$C_3$ alkyl.

In some embodiments, A can be a single bond, $L^2$ can be —(C=O)—, $R^4$ can be —(CH$_2$CH(R$^{4'}$)O)$_y$—R$^{4'}$, and y can be from 1 to 10. In some embodiments, A can be a single bond, $L^2$ can be —(C=O)—, $R^4$ can be —(CH$_2$CH$_2$O)$_y$—R$^{4'}$, y can be from 1 to 10, and $R^{4'}$ can be optionally substituted $C_1$-$C_3$ alkyl.

Examples of polymers of formula (V) include, but are not limited to, Poly(vinylether)s, Poly(methylvinylether) (PMVEth), Poly(2-methoxyethylvinylether) (PMOVEth), Poly(2-ethoxyethylvinylether) (PEOVEth), Poly(2-(2-ethoxy)ethoxyethylvinylether), Poly(4-hydroxybutylvinylether), Alkylglycidylethers: poly(methyl glycidyl ether), poly(ethyl glycidyl ether), and poly(ethoxyethyl glycidyl ether), Poly(vinylalcohol) PVAl, Poly(vinylacetate) PVAc, grafted polymethacrylates (molecular brushes), Poly[2-(2-ethoxyethoxyl)ethylacrylate] (PEEO2A), Poly[2-(2-methoxyethoxyl)ethylmethacrylate)] (PMEO2MA), Poly(2-[2-(2-methoxyethoxy)ethoxy]ethylmethacrylate) (PMEO3MA), Poly[oligo(ethyleneglycol)methacrylate](POEGMA), Poly(2-hydroxypropylacrylate) (PHPA), and Poly(2-hydroxyethylmethacrylate) (PHEMA).

In some embodiments, a temperature-responsive polymer includes a monomer unit of formula (VI):

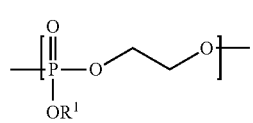

(VI)

In some embodiments, $R^1$ can be optionally substituted $C_1$-$C_6$ alkyl. In some embodiments, $R^1$ can be unsubstituted $C_1$-$C_6$ alkyl. In some embodiments, $R^1$ can be unsubstituted $C_1$-$C_3$ alkyl Examples of polymers of formula (VI) include, but are not limited to, Poly(phosphoester)s, Poly(2-ethoxy-2-oxo-1,3,2-dioxaphospholane), which can also be referred to as poly(ethyl ethylene phosphate), and Poly(2-isopropoxy-2-oxo-1,3,2-dioxaphospholane), which can also be referred to as poly(isopropyl ethylene phosphate).

In some embodiments, the temperature-responsive polymer can further include a monomer unit of formula (VII):

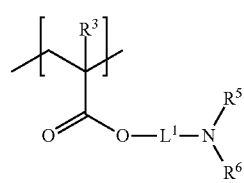

(VII)

wherein $L^1$ can be optionally substituted $C_1$-$C_8$ alkylene;
$R^5$ can be H or $C_1$-$C_3$ alkyl; and
$R^6$ can be H or

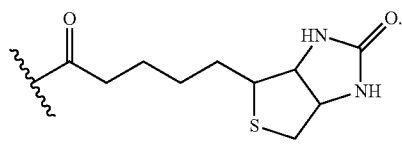 [SMILES: *C(=O)CCCCC1SCC2NC(=O)NC21]

In some embodiments, the temperature-responsive polymer can include a monomer unit having the formula:

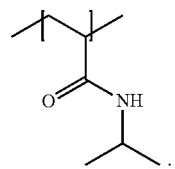

In some embodiments, the temperature-responsive polymer can be a copolymer that can include a first monomer unit having the formula:

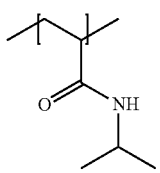

and a second monomer unit that can be suitable for attaching a cell-selective binding molecule thereto.

In some embodiments, the second monomer unit that can be suitable for attaching a cell-selective binding molecule thereto can have the formula

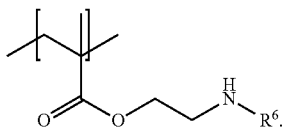

In some embodiments, the cell-selective binding molecule can be an antibody. In some embodiments, the antibody can be, but is not limited to, anti-EpCAM.

In some embodiments, the copolymer can include the first monomer unit and the second monomer unit in a proportion of about 0.1% to 10% of the second monomer unit. In some embodiments, the copolymer can include the first monomer unit and the second monomer unit in a proportion of about 2.5% to 10% of the second monomer unit.

In some embodiments, the copolymer can have chains with molecular weights in the range of about 4000 to 20,000 g/mol and a thickness in the range of about 6 nm to 30 nm.

In some embodiments, the device 100 can be used for isolating rare cells from bodily fluids and dissociated tissue, for example. When anti-EpCAM is grafted on polymer layers, the device can be employed to capture breast cancer cells from ascitic fluid collected from a metastatic breast cancer patient, for example. When anti-CA19-9 is grafted on the polymer layers, the device can be employed to capture pancreatic cancer cells from dissociated pancreatic cancer tissue (containing about 10% of cancer cells and 90% of stromal cells), for example. In some embodiments, single pancreatic cancer cells can be isolated for subsequent molecular and functional analysis. When a cocktail antibody reagent (e.g., anti-CD71 and anti-CD147) is grafted on the polymer layer, the device can be employed to capture fetal nucleated red blood cells (fNRBCs) from maternal blood at 6-15 week of pregnancy, for example.

Figure 2:
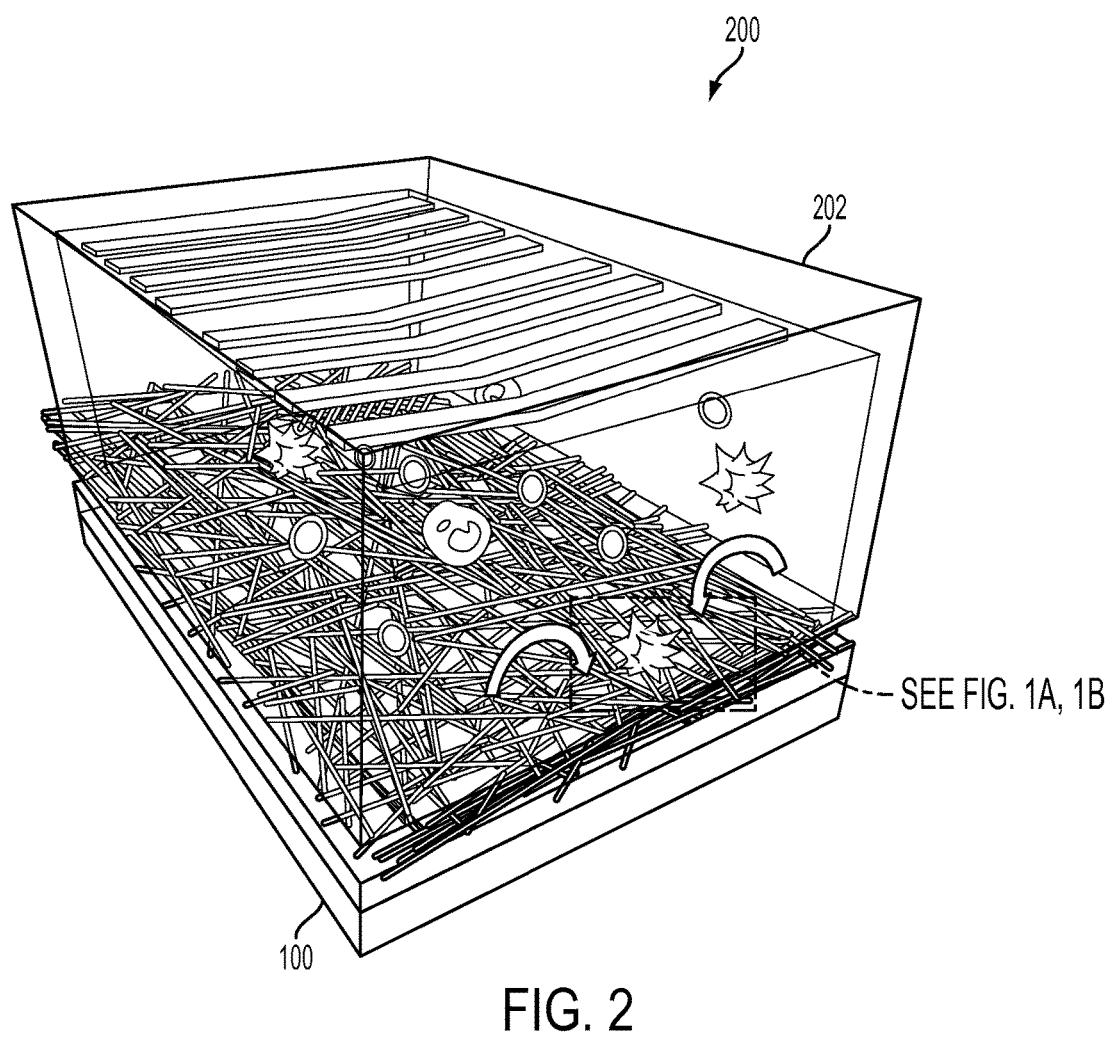
FIG. 2 shows an example of the device of FIGS. 1A and 1B incorporated into a fluidic chip according to an embodiment of the current invention. In this embodiment, an overlaid PolyDiMethylSiloxane (PDMS) chip with a serpentine chaotic mixing channel that encourages cell-substrate contact frequency is included. For CTC capture, the device is set at 37° C. Subsequently, a blood sample containing CTCs flows through the device, the herringbone micropatterns on the channel roof induce vertical flow in the microchannel. Consequently, the contact frequency between CTCs and the NanoVelcro substrate increases, resulting in enhanced CTC-capture efficiency. Once the CTCs are captured (immobilized) on the nanostructured substrate, the device can be set to 4° C., resulting in specific release of CTCs from the substrates.

In some embodiments, the device 100 can be incorporated into a fluidic chip, such as fluidic chip 200 illustrated schematically in FIG. 2. The fluidic chip 200 can include a channel-defining layer 202 fluidly sealed over device 100. The channel-defining layer 202 can be, but is not limited to, a PDMS layer, for example. The channel-defining layer 202 can define a serpentine path over the surface of the device 100 so as to cover a greater surface area. The channel-defining layer 202 can also include a chaotic mixer surface structure to prevent laminar flow and thus improve cell capture efficiency. In some embodiments, the fluidic chip 200 can be used in the system described in PCT/US13/43171 and incorporated herein by reference. However, the device 100 is not limited to being used in a fluidic chip. In other embodiments, a sample could be placed on the device 100, such as, but not limited to, a droplet. In such a case, the sample may not flow over the surface of the device 100. Other embodiments can include the device 100 being made to be dipped into a sample.

Figure 3:
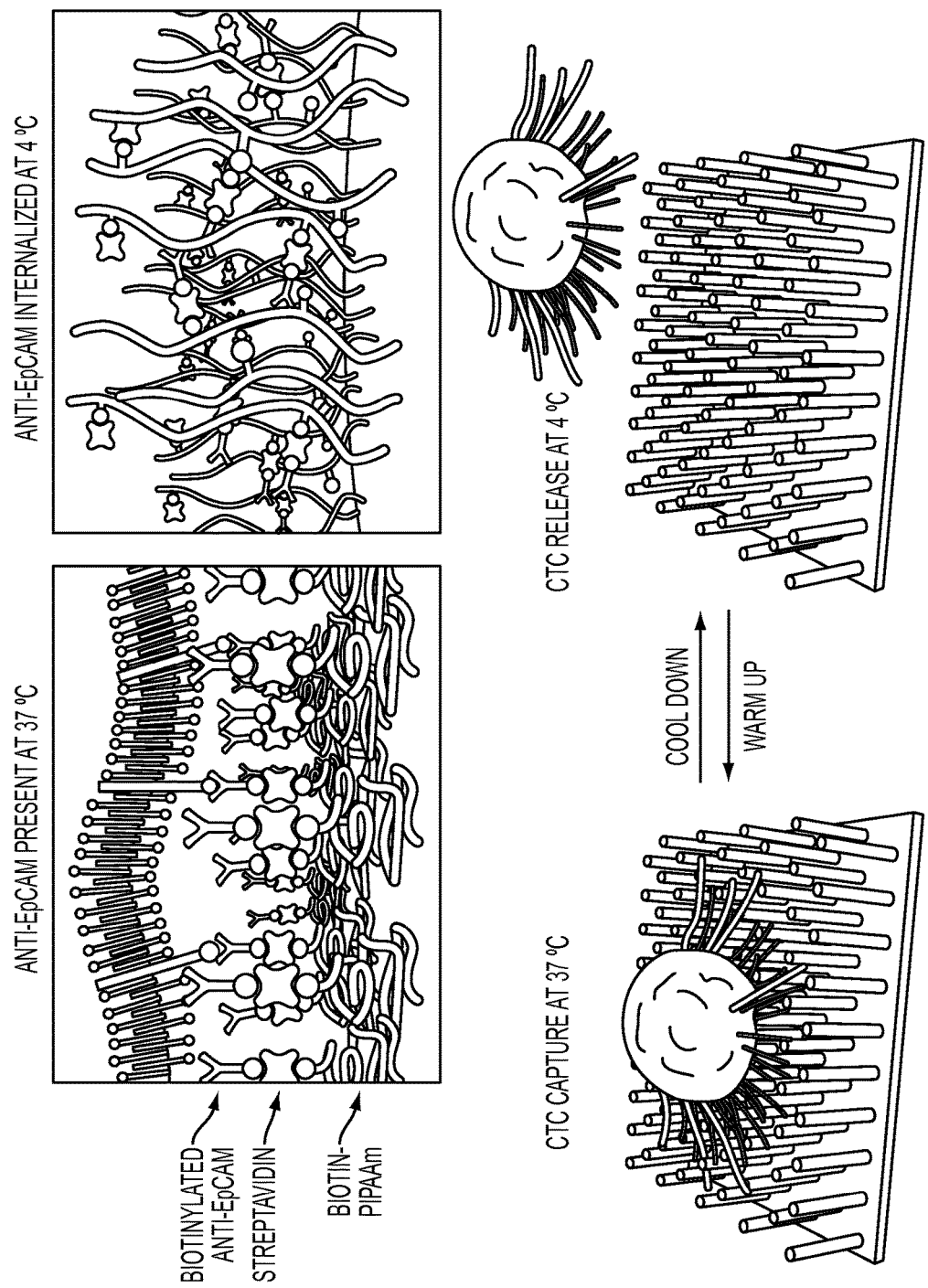
FIG. 3 is a schematic illustration to help explain some concepts of some embodiments of the current invention. In order to confer thermal responsiveness onto the NanoVelcro CTC assay in this example, biotin-functionalized polymer brushes (i.e., PIPAAm) are covalently grafted onto a silicon nanowire substrate (SiNWS). At 37° C., the biotin groups and hydrophobic domains of biotinylated PIPAAm are present on the surfaces of biotin-P-SiNWS. Via Biotin-streptavidin interaction, biotinylated anti-EpCAM can be introduced onto biotin-P-SiNWS, enabling highly efficient CTC capture. When the temperature is cooled down to 4° C., the backbones of surface-grafted biotinylated PIPAAm expand, resulting in CTC release from the substrates.

FIG. 3 provides a schematic illustration to help explain the operation of the device 100. In this example, the temperature-responsive material is in a compact configuration at 37° C. This configuration allows an increased number of the anti-EpCAM to be available for binding to the CTC in addition to the physical VELCRO-like attachment to the CTC. As the temperature is lowered to 4° C., the temperature-responsive material takes on an expanded configuration. Since the anti-EpCAM is attached along the polymer chain, the expansion results in many of the anti-EpCAM attachments to the CTC to break free, thus facilitating removal of the CTC in a viable condition.

EXAMPLES

The following examples help explain some concepts of the current invention. However, the general concepts of the current invention are not limited to the particular examples.

Some embodiments of the current invention provide a nanostructured device with a layer of temperature responsive material, as follows. The concept in this example is to covalently graft thermally responsive polymer brushes, poly (N-isopropylacrylamide (PIPAAm), onto SiNWS (FIGS. 1A, 1B, 3 and 4A) by a surface initiated atom-transfer radical polymerization (polymer grafted SiNWS will be abbreviated as P-SiNWS).[13] In these polymer brushes, we strategically introduced a covalently-linked biotin group by polymerizing isopropylacrylamide containing a small portion (2.5-10%) of methyl aminoethylmethacrylate. The amino groups on the polymer brushes were then conjugated directly with activated biotin (biotin-NHS) to form biotin-P-SiNWS. At 37° C., the biotin groups and hydrophobic domains of these polymers are present on the surfaces of biotin-P-SiNWS. Through a biotin-streptavidin interaction, the capture agent (i.e., biotinylated anti-EpCAM in this example) can be introduced onto the substrates, enabling a highly efficient CTC capture that is comparable to that observed for the NanoVelcro cell-affinity assay.[8] When the temperature is reduced to 4° C., the backbones of substrate-grafted PIPAAm undergo conformational changes, leading to an internalization of anti-EpCAM embedded inside the elongated polymer brushes. As a result, the nanosubstrate-immobilized CTCs are effectively released. PIPAAm[14] is a well-established biocompatible polymer, which can reversibly bind and release cells due to the thermally responsive switch of its surface properties. One of the most powerful utilities of a PIPAAm-grafted substrate is "Cell-Sheet" technology, where cells adhere to the hydrophobic domains of PIPAAm at 37° C., followed by growing into confluency.[15] The substrates are then cooled down to below PIPAAm's lower critical solution temperature (e.g., 4° C.) to induce its surface hydrophobic-to-hydrophilic switch, allowing detachment of confluently cultured cells from the substrates to produce a "cell sheet".[16] Clearly, PIPAAm's operation temperature ensures minimum disruption to cells' viability and functions during their seeding and releasing process.[17] When using biotin-P-SiNWS to capture and release CTCs, we will demonstrate that the same advantages do apply.

Figures 4A, 4B, 4C:
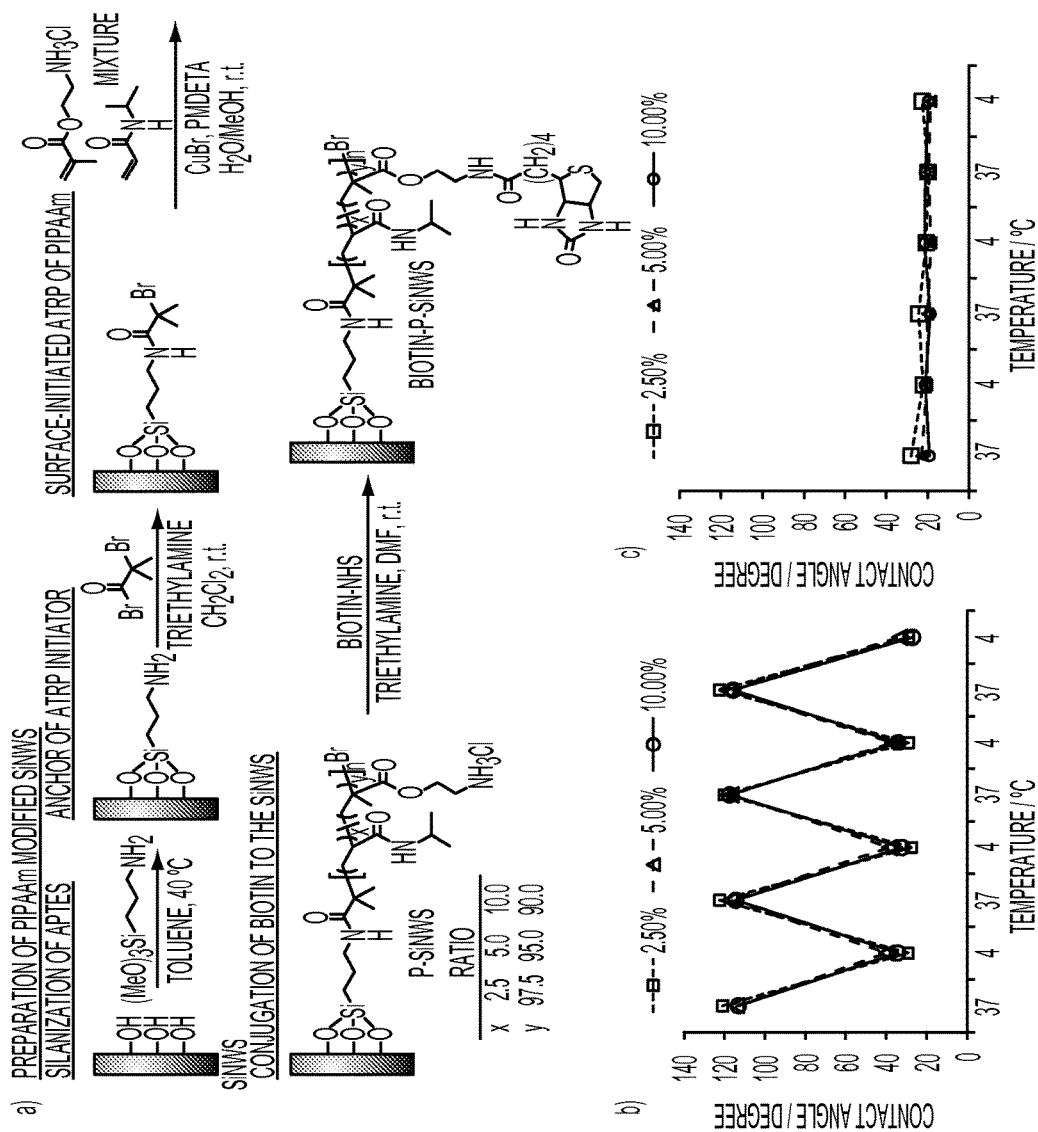
FIGS. 4A-4C show a) a synthetic approach employed to covalently graft biotinylated PIPAAm onto SiNWS. By altering the ratios of the two monomeric precursors, three different densities (2.5, 5 and 10%) of biotin groups were incorporated onto the resulting biotin-P-SiNWS. b) Contact angles were employed to examine thermal responsiveness of the three biotin-P-SiNWS. c) After introducing anti-EpCAM onto biotin-P-SiNWS, the surface becomes hydrophilic no matter what temperatures were applied.

The biotin-P-SiNWS were prepared as illustrated in FIG. 4A. First, we fabricated densely packed SiNWS with diameters of 100-200 nm and lengths of 15-20 µm on silicon wafers using a wet chemical etching method. Onto these SiNWS, an aminosiloxane mono-layer was assembled and the initiator for atom transfer radical polymerization (ATRP)

was introduced through covalent amide linkage. Surface initiated ATRP was carried out with a mixture of isopropylacrylamide and methyl aminoethylmethacrylate to yield grafted polymer brushes. The polymerization was carried out for 6 hours because it was necessary to obtain polymers across certain length threshold to confirm the thermal response. The polymerization could not take place too long, otherwise the nanostructures could be lost. The molecular weight of these polymer brushes was 8800 g/mol and the thickness was estimated as 14 nm.[18] Biotin moieties were then conjugated to the free amino groups of these polymer brushes to yield the desired biotin-P-SiNWS. Three biotin-P-SiNWS with functional group densities of 2.5, 5, and 10% were prepared and temperature-dependent contact angle measurements of water droplets were utilized to examine the thermoresponsive surface properties of these biotin-P-SiNWS. As shown in FIG. 4B, all three biotin-P-SiNWS underwent reversible switches between hydrophobic and hydrophilic surfaces at 37 and 4° C., respectively. There were only minute differences observed with respect to their biotin densities. To examine the effect of biotin densities on the cell capture and release performance, biotinylated anti-EpCAM (10 µg/mL) was introduced onto biotin-P-SiNWS containing 2.5, 5, and 10% biotin moiety via streptavidin conjugation (40 µg/mL). After the antibody introduction, the surfaces became hydrophilic at 37° C. (FIG. 4C) and the surfaces no longer switched between hydrophobic and hydrophilic when the temperature changed. This is due to the charged antibody on the surface. However, thermoresponsiveness of the polymer brushes should remain as illustrated in FIG. 3 because of the same backbone movement of PIPAAm.

Figures 5A, 5B, 5C, 5D:
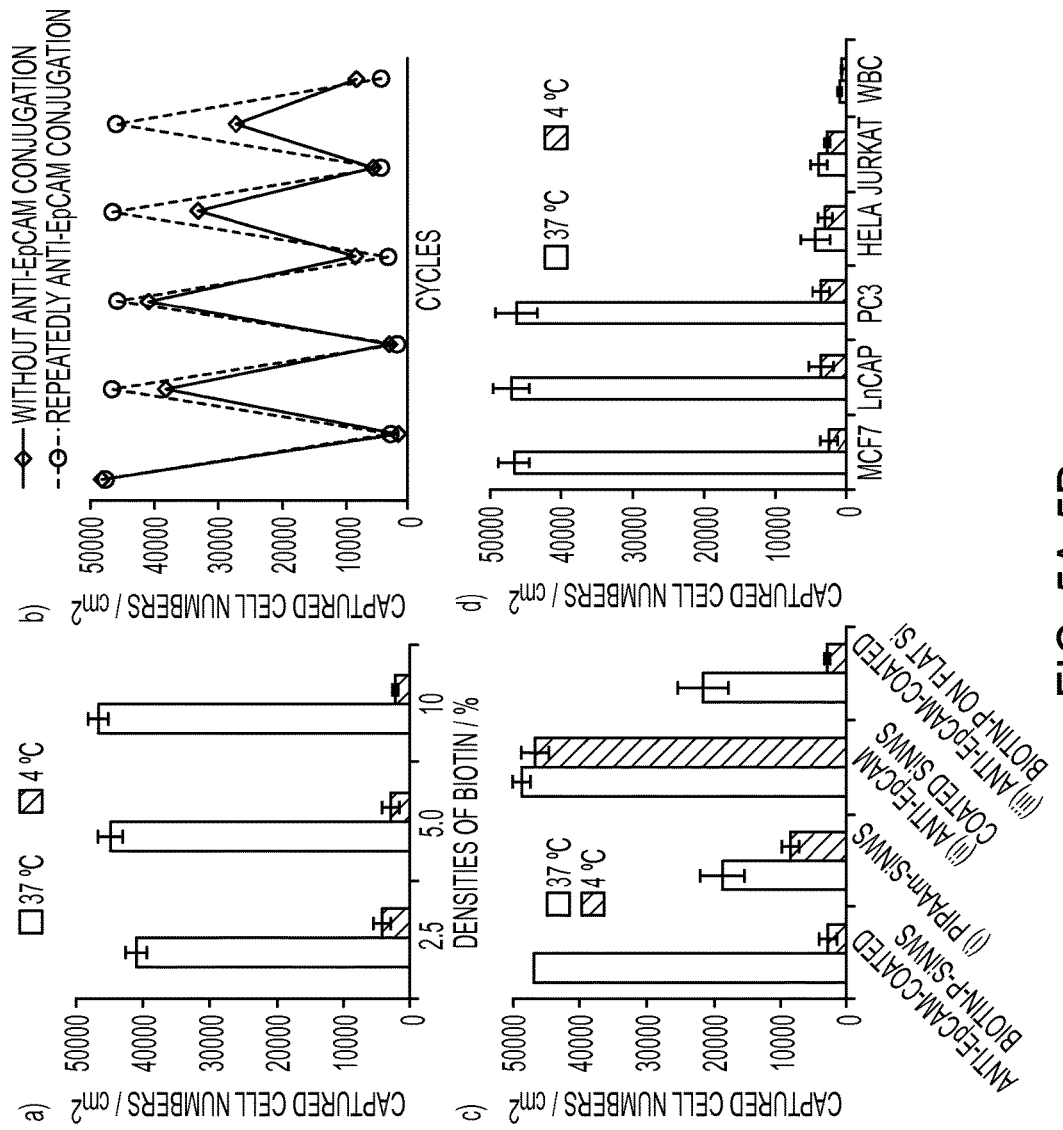
FIG. 5A-5D provide data to compare an embodiment of the current invention with alternative structures. a) Quantitative evaluations of cell capture/release performance of three biotin-P-SiNWS with different densities (2.5, 5 and 10%) of biotin groups. b) Cell capture/release performance of 10%-biotin-P-SiNWS in multiple/sequential rounds of studies w/wo repeated anti-EpCAM conjugation. c) Cell capture/release studies were conducted using three control samples: (i) PIPAAm-SiNWS, (ii) anti-EpCAM-coated SiNWS, and (iii) anti-EpCAM-coated biotin-P on flat Si chips, were examined in parallel with 10%-biotin-P-SiNWS. d) Quantitative evaluations of general applicability and specificity of 10%-biotin-P-SiNWS using three EpCAM-positive cancer-cell lines (i.e., MCF7, LnCAP and PC3 cancer cell lines), two EpCAM-negative cancer-cell lines (i.e., HeLa and Jurkat cell lines) and freshly isolated human white blood cells.
Figures 7A, 7B, 7C, 7D:
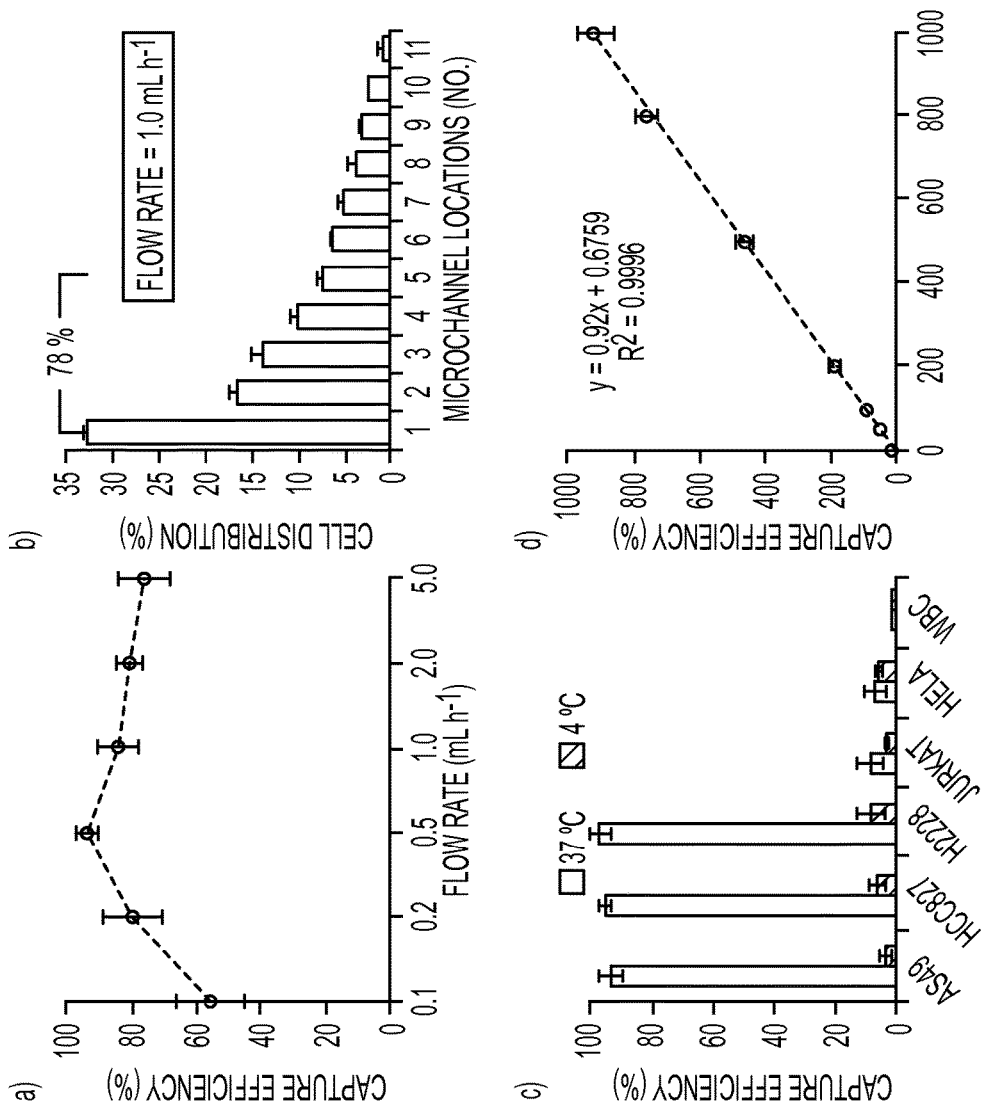
FIGS. 7A-7D provide data for a) Cell-capture efficiency of a thermoresponsive NanoVelcro CTC Chip according to an embodiment of the current invention at flow rates of 0.1, 0.2, 0.5, 1, 2, and 5 mL h-1. b) The distributions of captured cells on the thermoresponsive NanoVelcro Chips were assessed in PBS. The majority (78%) of CTCs are captured in the first 4 channels. c) Capture efficiencies of three different lung cancer cell lines (i.e., A549, HCC827, and H2228, expressing EpCAM) and control cells (Jurkat, Hela, and WBC, expressing no EpCAM) in PBS at both 37 and 4° C. All error bars show standard deviations (n>=3). d) Capture efficiencies at different spiking cell numbers ranging from 10-1000 cells mL-1.
Figures 8A, 8B, 8C:
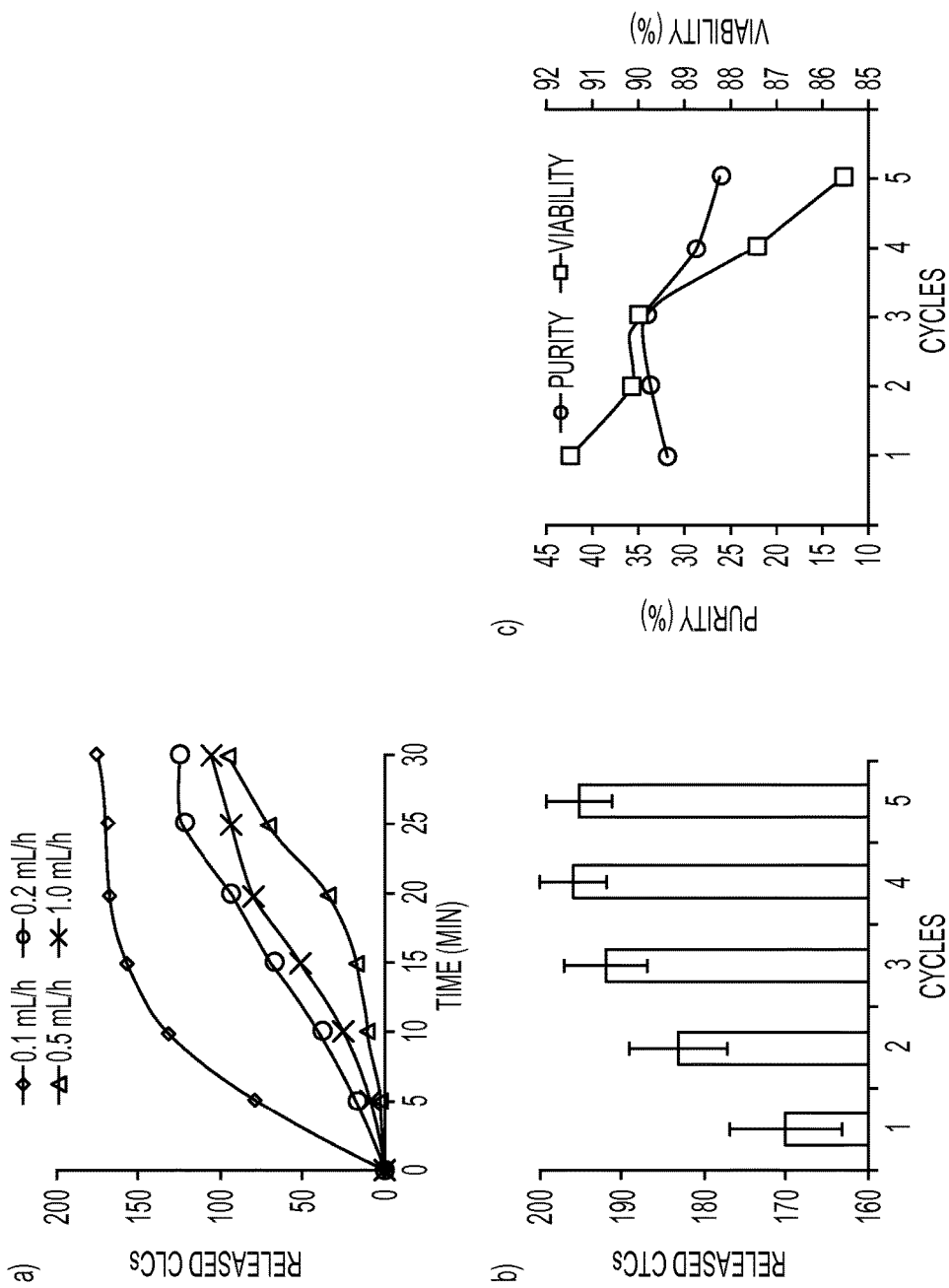
FIGS. 8A-8C provide data for a) CTC release performance as the function of flow rates and elution times. From these data, an optimal condition (flow rate: 0.1 mL/h and elution time: 20 min) is determined according to an embodiment of the current invention. b) Cell releasing performance can be enhanced by performing multiple cycles of heating and cooling between 37 and 4° C., respectively. Excellent cell-releasing performance can be achieved after 4-5 cycles of healing and cooling. We note that the experimental data was obtained by capturing about 200 CTCs in the next-generation thermoresponsive NanoVelcro CTC Chips according to an embodiment of the current invention. After the given heating/cooling cycles, CTCs are collected and counted in the eluents flowing out of the next-generation thermoresponsive NanoVelcro CTC Chips. c) CTC purity and viability as the function of heating/cooling cycles. Although multiple heating/cooling cycles help CTC release performance, cell viability and purity is somehow compromised.

To study cell capture performance of the thermoresponsive NanoVelcro cell-affinity assay, a cell suspension ($10^5$ cells mL$^{-1}$) containing an EpCAM-positive breast-cancer cell line (i.e., MCF7) in a DMEM medium was prepared and then introduced onto anti-EpCAM-coated biotin-P-SiNWS (1×2 cm, placed into a commercial cell chamber slide), followed by 30-min incubation (5% $CO_2$, 37° C.). After rinsing, the substrate-immobilized cells (pre-stained with DiO green fluorescent dye) were imaged and counted by a fluorescence microscope (Nikon, 90i). Successively, cell release studies were carried out by the aforementioned chamber slide (with immobilized MCF7 cells on anti-EpCAM coated substrates) in a 4° C. refrigerator for 30 min. The remaining MCF7 cells on the substrates were then quantified. The results summarized in FIG. 5A suggest biotin-P-SiNWS containing 10% biotin displayed the highest cell-capture performance at 37° C., whereas the lowest cell retention was also observed at 4° C. Given the optimal cell capture/release performance, we therefore focused our further characterization and optimization studies on biotin-P-SiNWS with 10% biotin. To test this substrate for repeated capture and release of cells, we performed multiple cycles of studies in sequence using MCF7 cells again. We observed a gradually attenuated cell capture/release performance (see solid line in FIG. 5B) with an increasing number of experimental cycles. We hypothesize that the capture agent, anti-EpCAM, could dissociate from the polymer brushes as a result of its thermally responsive conformation changes during the capture/release processes. To validate this hypothesis, we repeatedly conducted anti-EpCAM conjugation prior to cell capture/release studies. By doing so the cell capture/release performances in new cycles were restored (see dashed line in FIG. 5B).

It is unique that our platform integrates three different features for capture and release of cells. To validate the individual contribution of anti-EpCAM-coated biotin-P-SiNWS (10% of biotin) to the performance, three control studies were conducted using (i) PIPAAm-SiNWS: no capture agent to examine how temperature-induced conformational changes of PIPAAm contribute to cell capture/release, (ii) anti-EpCAM-coated SiNWS: no thermal responsiveness as the original NanoVelcro cell-affinity assay, and (iii) anti-EpCAM-coated biotin-P on flat Si chips (no nanostructures). The results summarized in FIG. 5C suggested that all three factors (capture agent, thermally responsive polymer brushes and nanostructures) play significant roles in achieving the enhanced cell capture/release performance, supporting conceptual description (FIG. 3). In the case of PIPAAm-SiNWS and anti-EpCAM-coated biotin-P on flat Si chips, the capture efficiency was lower. On the other hand, established anti-EpCAM-coated SiNWS[8] showed similar capture efficiencies with anti-EpCAM-coated biotin-P-SiNWS. However, these bound cells remained attached to the surface when the surface was cooled to 4° C. Finally, we tested the general applicability and specificity of biotin-P-SiNWs for capturing EpCAM-positive cancer cells. Three EpCAM-positive cancer-cell lines (MCF7 cells, LnCAP and PC3 prostate cancer cells) were studied in parallel with two EpCAM-negative cancer-cell lines (HeLa cervical cancer cells and Jurkat leukemia cells) and freshly isolated human white blood cells (WBCs). Summarized results in FIG. 5D suggested that, anti-EpCAM-coated biotin-P-SiNWS were capable of specifically capturing and releasing EpCAM-positive cancer cells. On the contrary, relatively low cell numbers were observed for EpCAM-negative cells (i.e., HeLa and Jaket), as well as human WBCs.

To test the dynamic rage of the thermoresponsive NanoVelcro cell-affinity assay, a series of artificial CTC blood samples was prepared by spiking DMEM medium and heath donors' blood with DiO-stained MCF7 cells at densities of 10, 50, 100, 500 and 1,000 cells per mL of blood. The results are summarized in FIG. 6A. Anti-EpCAM-coated biotin-P-SiNWS shows vastly improved capture yields (>70%), similar to those observed for the previously demonstrated anti-EpCAM-coated SiNWS[8]. Most importantly, anti-EpCAM-coated biotin-P-SiNWS is capable of capture and release viable cancer cells. When 1,000 MCFs cells are subjected for CTC capture studies, more than 90% cell can be captured (at 37° C.) and released (at 4° C.) from the substrates (white bar, FIG. 6B). Further, approximately 90% of the released cells remained viable (white bar, FIG. 6B), and they can be further expanded in culture (FIG. 6C). In contrast, cells can be captured efficiently on anti-EpCAM-coated SiNWS while trypsin-treated cell release led to moderate cell-release performance and poor cell viability (black bars, FIG. 6B).

In conclusion, we demonstrated an innovative cell capture and release platform according to an embodiment of the current invention with integrated features of capture-agent directed specific recognition, nanostructure amplified cell capturing, and stimulated cell release based on thermally responsive polymer brushes. This platform can demonstrate superior performances in (1) capturing cancer cells with high efficiency at 37° C., and (2) releasing the captured cancer cells with great viability and retained functionality at 4° C. Both features enable isolation of circulating tumor cells (CTCs) with minimum contamination of the surrounding white blood cells (WBCs) and negligible disruption to CTCs' viability and functions, thus providing a useful tool for molecular and functional analyses of CTCs. It is conceivable that the CTC-derived molecular signatures and functional readouts may provide valuable insight into tumor biology during the critical window where therapeutic intervention could make a significant difference.

REFERENCES

[1] K. Pantel, C. Alix-Panabieres, *Trends Mol Med* 2010, 16, 398-406.
[2] K. Pantel, R. H. Brakenhoff, *Nat Rev Cancer* 2004, 4, 448-456.
[3] K. Pantel, R. H. Brakenhoff, B. Brandt, *Nat Rev Cancer* 2008, 8, 329-340.
[4] aE. Racila, D. Euhus, A. J. Weiss, C. Rao, J. McConnell, L. W. M. M. Terstappen, J. W. Uhr, *Proceedings of the National Academy of Sciences of the United States of America* 1998, 95, 4589-4594; bV. Zieglschmid, C. Hollmann, O. Bocher, *Crit Rev Clin Lab Sci* 2005, 42, 155-196.
[5] aM. Cristofanilli, G. T. Budd, M. J. Ellis, A. Stopeck, J. Matera, M. C. Miller, J. M. Reuben, G. V. Doyle, W. J. Allard, L. W. Terstappen, D. F. Hayes, *N Engl J Med* 2004, 351, 781-791; bS. Riethdorf, H. Fritsche, V. Muller, T. Rau, C. Schindlbeck, B. Rack, W. Janni, C. Coith, K. Beck, F. Janicke, S. Jackson, T. Gornet, M. Cristofanilli, K. Pantel, *Clin Cancer Res* 2007, 13, 920-928; cD. R. Shaffer, M. A. Leversha, D. C. Danila, O. Lin, R. Gonzalez-Espinoza, B. Gu, A. Anand, K. Smith, P. Maslak, G. V. Doyle, L. W. Terstappen, H. Lilja, G. Heller, M. Fleisher, H. I. Scher, *Clin Cancer Res* 2007, 13, 2023-2029.
[6] aS. Nagrath, L. V. Sequist, S. Maheswaran, D. W. Bell, D. Irimia, L. Ulkus, M. R. Smith, E. L. Kwak, S. Digumarthy, A. Muzikansky, P. Ryan, U. J. Balis, R. G. Tompkins, D. A. Haber, M. Toner, *Nature* 2007, 450, 1235-1239; bA. A. Adams, P. I. Okagbare, J. Feng, M. L. Hupert, D. Patterson, J. Gottert, R. L. McCarley, D. Nikitopoulos, M. C. Murphy, S. A. Soper, *J Am Chem Soc* 2008, 130, 8633-8641; cS. L. Stott, C. H. Hsu, D. I. Tsukrov, M. Yu, D. T. Miyamoto, B. A. Waltman, S. M. Rothenberg, A. M. Shah, M. E. Smas, G. K. Korir, F. P. Floyd, Jr., A. J. Gilman, J. B. Lord, D. Winokur, S. Springer, D. Irimia, S. Nagrath, L. V. Sequist, R. J. Lee, K. J. Isselbacher, S. Maheswaran, D. A. Haber, M. Toner, *Proc Natl Acad Sci USA* 2010, 107, 18392-18397; dJ. P. Gleghorn, E. D. Pratt, D. Denning, H. Liu, N. H. Bander, S. T. Tagawa, D. M. Nanus, P. A. Giannakakou, B. J. Kirby, *Lab Chip* 2010, 10, 27-29; eU. Dharmasiri, S. K. Njoroge, M. A. Witek, M. G. Adebiyi, J. W. Kamande, M. L. Hupert, F. Barany, S. A. Soper, *Anal Chem* 2011, 83, 2301-2309; fM. N. Dickson, P. Tsinberg, Z. L. Tang, F. Z. Bischoff, T. Wilson, E. F. Leonard, *Biomicrofluidics* 2011, 5; gS. Wang, K. Liu, J. Liu, Z. T. Yu, X. Xu, L. Zhao, T. Lee, E. K. Lee, J. Reiss, Y. K. Lee, L. W. Chung, J. Huang, M. Rettig, D. Seligson, K. N. Duraiswamy, C. K. Shen, H. R. Tseng, *Angew Chem Int Ed Engl* 2011, 50, 3084-3088.
[7] P. T. H. Went, A. Lugli, S. Meier, M. Bundi, M. Mirlacher, G. Sauter, S. Dimhofer, *Human Pathology* 2004, 35, 122-128.
[8] S. Wang, H. Wang, J. Jiao, K. J. Chen, G. E. Owens, K. Kamei, J. Sun, D. J. Sherman, C. P. Behrenbruch, H. Wu, H. R. Tseng, *Angew Chem Int Ed Engl* 2009, 48, 8970-8973.
[9] aK. E. Fischer, B. J. Aleman, S. L. Tao, R. H. Daniels, E. M. Li, M. D. Bunger, G. Nagaraj, P. Singh, A. Zettl, T. A. Desai, *Nano Letters* 2009, 9, 716-720; bA. S. G. Curtis, M. Varde, *Journal of the National Cancer Institute* 1964, 33, 15-&; cW. F. Liu, C. S. Chen, *Advanced Drug Delivery Reviews* 2007, 59, 1319-1328.
[10] J. Sekine, S. C. Luo, S. Wang, B. Zhu, H. R. Tseng, H. H. Yu, *Adv Mater* 2011, 23, 4788-4792.
[11] N. Zhang, Y. Deng, Q. Tai, B. Cheng, L. Zhao, Q. Shen, R. He, L. Hong, W. Liu, S. Guo, K. Liu, H.-R. Tseng, B. Xiong, X.-Z. Zhao, *Adv Mater* 2012, 24, in press.
[12] aL. Chen, X. Liu, B. Su, J. Li, L. Jiang, D. Han, S. Wang, *Adv Mater* 2011, 23, 4376-4380; bD. J. Kim, J. K. Seol, Y. Wu, S. Ji, G. S. Kim, J. H. Hyung, S. Y. Lee, H. Lim, R. Fan, S. K. Lee, *Nanoscale* 2012, 4, 2500-2507.
[13] L. Chen, M. Liu, H. Bai, P. Chen, F. Xia, D. Han, L. Jiang, *Journal of the American Chemical Society* 2009, 131, 10467-10472.
[14] aT. Okano, N. Yamada, M. Okuhara, H. Sakai, Y. Sakurai, *Biomaterials* 1995, 16, 297-303; bJ. E. Chung, M. Yokoyama, M. Yamato, T. Aoyagi, Y. Sakurai, T. Okano, *Journal of Controlled Release* 1999, 62, 115-127.
[15] K. Nishida, M. Yamato, Y. Hayashida, K. Watanabe, K. Yamamoto, E. Adachi, S. Nagai, A. Kikuchi, N. Maeda, H. Watanabe, T. Okano, Y. Tano, *New England Journal of Medicine* 2004, 351, 1187-1196.
[16] Y. Kumashiro, M. Yamato, T. Okano, *Annals of Biomedical Engineering* 2010, 38, 1977-1988.
[17] Q. Yu, Y. Zhang, H. Chen, F. Zhou, Z. Wu, H. Huang, J. L. Brash, *Langmuir* 2010, 26, 8582-8588.
[18] E. Turan, S. Demirci, T. Caykara, *Thin Solid Films* 2010, 518, 5950-5954.

The embodiments illustrated and discussed in this specification are intended only to teach those skilled in the art how to make and use the invention. In describing embodiments of the invention, specific terminology is employed for the sake of clarity. However, the invention is not intended to be limited to the specific terminology so selected. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

We claim:

1. A device for capturing preselected cell types from a fluid sample comprising a plurality of cell types, comprising:
    a substrate;
    a plurality of nanowires at least one of attached to or integral with a surface of said substrate such that each nanowire of said plurality of nanowires has an unattached end;
    a layer of temperature-responsive material formed on at least said unattached end of each of said plurality of nanowires; and
    at least one type of cell-selective binding molecule attached to a plurality of portions of said layer of temperature-responsive material,
    wherein said layer of temperature-responsive material has a compact configuration at a first temperature and an expanded configuration at a second temperature so as to facilitate release of cells captured at said first temperature to be released at said second temperature,
    wherein the first temperature is greater than the second temperature,
    wherein said first temperature is greater than 0° C. and less 100' C, and said second temperature is greater 0° C. and less 100° C.,
    wherein said layer of temperature-responsive material formed on at least said unattached end of each of said plurality of nanowires comprises a temperature-responsive polymer, wherein said temperature-responsive polymer comprises a copolymer comprising a first monomer unit having the formula:

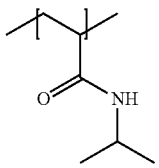

and a second monomer unit that is suitable for attaching a cell-selective binding molecule thereto, wherein said second monomer unit that is suitable for attaching a cell-selective binding molecule thereto has a formula:

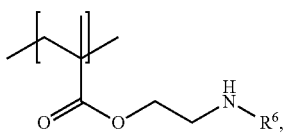

where $R^6$ is H or

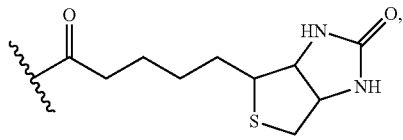

wherein the first monomer unit is in a proportion of about 0.1% to 10% of the second monomer unit, and wherein a combination of said plurality of nanowires, said layer of temperature-responsive material, and said at least one type of cell-selective binding molecule attached to said plurality of portions of said layer of temperature-responsive material provide a cell capture yield of at least 70% and a cell viability rate following release of at least 20%.

2. The device for capturing preselected cell types according to claim 1, wherein said first temperature is within a range of temperatures to maintain viability of captured and released cells, and wherein said second temperature is within the range of temperatures to maintain viability of the captured and released cells.

3. The device for capturing preselected cell types according to claim 1, wherein each of said plurality of nanowires has an average diameter that is less than 500 nanometers.

4. The device for capturing preselected cell types according to claim 1, wherein each of said plurality of nanowires has an average diameter that is less than 250 nanometers and greater than 20 nanometers.

5. The device for capturing preselected cell types according to claim 1, wherein each of said plurality of nanowires has an average diameter that is within the inclusive range of 200 nanometers to 100 nanometers.

6. The device for capturing preselected cell types according to claim 1, wherein said at least one type of cell-selective binding molecule is attached to said layer of temperature-responsive material by at least one of biotin or streptavidin conjugation.

7. The device for capturing preselected cell types according to claim 1, wherein said cell-selective binding molecule binds to circulating cancer cells (CTCs).

8. The device for capturing preselected cell types according to claim 1, wherein said cell-selective binding molecule comprises an antibody.

9. The device for capturing preselected cell types according to claim 8, wherein said antibody comprises at least one of EpCAM, CA19-9, CD146, or CD147 antibodies for the capture of CTCs.

10. The device for capturing preselected cell types according to claim 1, wherein said cell-selective binding molecule binds to fetal nucleated red blood cells (fNRBCs) from maternal blood.

11. The device for capturing preselected cell types according to claim 8, wherein said antibody comprises at least one of CD71 or CD147 antibodies for the capture of fetal nucleated red blood cells (fNRBCs) from maternal blood.

12. The device for capturing preselected cell types according to claim 1, wherein the temperature-responsive polymer is covalently grafted to at least said unattached end of each of said plurality of nanowires.

13. The device for capturing preselected cell types according to claim 1, wherein said cell-selective binding molecule comprises an antibody.

14. The device for capturing preselected cell types according to claim 13, wherein said antibody is anti-EpCAM.

15. The device for capturing preselected cell types according to claim claim 1, wherein said copolymer has a molecular weight in a range of about 4,000 to 20,000 g/mol and a thickness in a range of about 6 nm to 30 nm.

16. The device for capturing preselected cell types according to claim 1, wherein said first temperature is about 37° C. and said second temperature is about 4° C.

* * * * *